United States Patent
De Vaughn et al.

(10) Patent No.: US 6,245,559 B1
(45) Date of Patent: Jun. 12, 2001

(54) HANDLE FOR INOCULATING LOOP (75) Inventors: Donald H. De Vaughn, San Francisco; Wolfgang Ott, Walnut Creek, both of CA (US)

(73) Assignee: Bio-Plas, Inc., San Francisco, CA (US)

( * ) Notice: Subject to any disclaimer, the term of this patent is extended or adjusted under 35 U.S.C. 154(b) by 0 days.

(21) Appl. No.: 09/677,614

(22) Filed: Oct. 3, 2000

(51) Int. Cl.[7] ....................................... C12M 1/26
(52) U.S. Cl. .................. 435/309.3; 73/864.72; 73/864.16; 422/100
(58) Field of Search .................. 73/864.72, 864.13, 73/864.16; 435/309.1, 309.2, 309.3; 422/100; 604/38, 187, 208

(56) References Cited

U.S. PATENT DOCUMENTS 3,742,187 * 6/1973 Folus ..................... 422/100
5,330,899   7/1994 De Vaughn .
5,650,124 * 7/1997 Gilson ..................... 422/100

* cited by examiner

*Primary Examiner*—David A. Redding
(74) *Attorney, Agent, or Firm*—Flehr Hohbach Test Albritton & Herbert LLP (57) ABSTRACT

A two-piece handle assembly (10, 10a) including a plunger (12, 12a) and a body (24, 24a) having an axial bore (50, 50a) in which plunger (12, 12a) can move between retracted and extended positions. The upper end (28) of body (24, 24a) includes a pair of opposed longitudinal slots (32) that permit radially outward resilient movement of the upper end (28) to enlarge a bore (52), defined by a neck portion (54) of the body, to permit insertion of plunger (12) into body (24, 24a). A plunger shoulder (44) is designed to engage a body shoulder (55) to limit movement of the plunger in the direction of retraction, and a finger pad (13) is provided to limit movement of the plunger in the direction of extension.

19 Claims, 6 Drawing Sheets

HANDLE FOR INOCULATING LOOP

TECHNICAL FIELD

The present invention relates to inoculation devices and, more particularly, to a handle apparatus for sanitary manipulation and control of inoculation loops during inoculation procedures.

BACKGROUND ART

In traditional laboratory inoculation techniques, as discussed in prior U.S. Pat. No. 5,330,899, entitled "Calibrated Inoculation Assembly and Method of Preserving Sterility," after a desired microorganism has been successfully incubated in a nutrient broth substance, it is necessary to further colonize the microorganism so that a particular strain can be identified and researched. For this, a predetermined quantity of inoculant from the broth is extracted and implanted in a nutrient medium so that the microorganism can be grown under controlled conditions.

A common tool used to inoculate the nutrient medium is an inoculation loop, which includes a loop end that carries the inoculant solution to the nutrient medium. A handle device is releasably coupled to the opposite end of the inoculation loop in order to allow the researcher to grasp and manipulate the inoculation loop in a sanitary, controlled manner while performing the inoculation procedures. Once used, an inoculation loop is disposed of, while the handle is re-used to perform additional inoculation procedures.

Typical prior art handles have been undesirably complex and costly to fabricate, requiring a multiplicity of injection molded and metal parts to fabricate and an undesirable amount of time to assemble.

Accordingly, it is an object of the present invention to simplify the design of an inoculation loop handle in order to reduce its fabrication cost, while still maintaining its functionality and ease of use.

DISCLOSURE OF INVENTION

Briefly described, the inoculation loop assembly of the present invention is formed as a two-piece assembly, which reduces the molding cost and greatly simplifies assembly. The device comprises an elongated body having an upper end and a lower end and an axial bore therethrough, and an elongated plunger mounted for longitudinal movement within the axial bore of the body between an extended position and a retracted position. The plunger includes an upper end extending exteriorly of the upper end of the body with a finger pad thereon. The plunger further includes a plunger shoulder spaced from the finger pad along the length of the plunger, which cooperates with a body shoulder to limit plunger movement. The body includes a resilient, slotted upper end formed for outward displacement of the adjacent body portions to permit enlargement of the axial bore at the upper end of the body for insertion of the lower end of the plunger into the axial bore and advancement of the plunger in the bore to its normal operating range. A narrow diameter length of the plunger provides a plunger shoulder for engaging the body shoulder to limit movement of the plunger outwardly beyond its retracted position. The finger pad of the plunger is adapted to engage the upper end of the body to limit inward movement of the plunger beyond its extended position.

According to an aspect of the invention, the plunger is a one piece monolithically formed member and the body is a one piece monolithically formed member. Monolithic formation of the two-piece assembly reduces manufacturing and assembly costs while still retaining reliable loop mounting, manipulation, and ejection.

According to another aspect of the invention, the narrow diameter section of the body is a neck portion at the upper end of the body, and the axial bore is formed with a diameter from the neck portion to the lower end adapted to permit removal of an injection molding core pin from the lower end of the body.

According to still another aspect of the invention, the body includes at least one radial hole extending through the body to the axial bore thereof Preferably, a plurality of radial holes are provided, each extending through the body to the axial bore thereof, and the plurality of radial holes are equally spaced along the length of the body in order to promote even and rapid cooling of the body mass after injection molding and after autoclaving.

These and other features, objects, and advantages of the present invention will become apparent from the following description of the Best Mode of Carrying Out the Invention, when read in conjunction with the accompanying drawings, and the claims, which are all incorporated herein as part of the disclosure of the invention.

BRIEF DESCRIPTION OF THE DRAWINGS

Throughout the several views, like reference numerals refer to like parts, wherein.

BEST MODE OF CARRYING OUT THE INVENTION

Reference will now be made in detail to the preferred embodiment of the invention, examples of which are illustrated in the accompanying drawings. While the invention will be described in conjunction with the preferred embodiment, it will be understood that the described embodiment is not intended to limit the invention specifically to those embodiments. On the contrary, the invention is intended to cover alternatives, modifications and equivalents, which may be included within the spirit and scope of the invention as defined by the appended claims.

Figure 1:
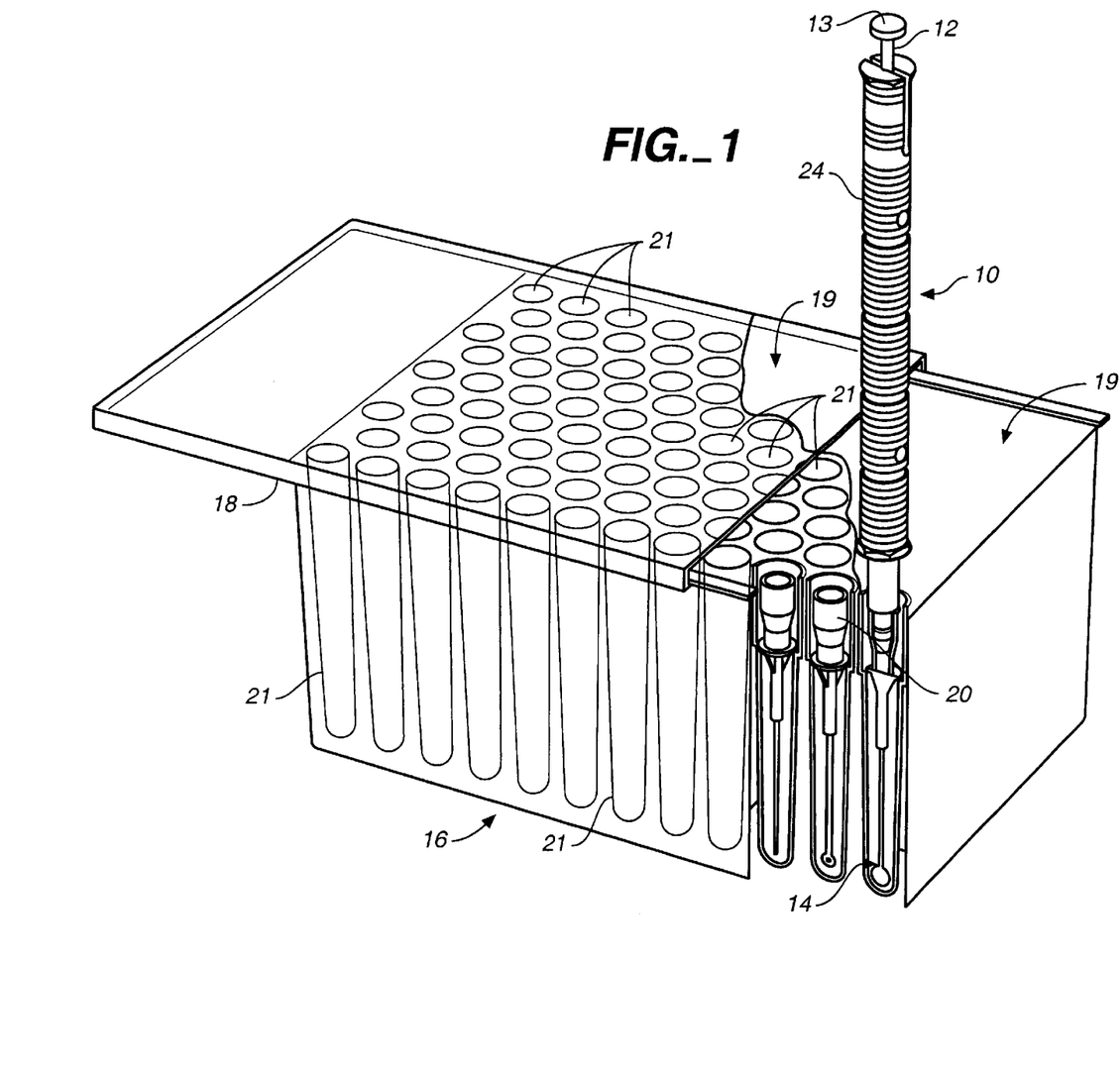
FIG. 1 is a partially broken away pictorial view of an inoculation loop rack with a set of inoculation loops therein and a protective membrane broken away to show the loop-receiving pockets and with the handle of the present invention engaging one of the inoculation loops for retrieval from the rack.

Referring to FIG. 1, the improved inoculation loop handle of the present invention is designated generally by reference numeral 10. As described in more detail herein, handle 10 is a two-piece assembly comprising an elongated generally cylindrical body 24 with an axial bore therein for receipt of an elongated plunger 12 having a transversely extending finger pad 13 at its upper end. Plunger 12 is longitudinally movable within the axial bore of body 24 between retracted and extended positions. A lower end of handle 10 is designed to engage and releasably secure a microorganism manipulation device, such as an inoculation loop 14, on the handle assembly. Loops 14 typically are sterilized and held in and dispensed from an inoculation loop rack 16 that includes a removable dust cover 18 and a thin frangible membrane 19 which covers the upper ends of the loop-receiving pockets or tubes 21 for providing easy access while maintaining sterility.

The design of inoculation loops 14 is described in detail in U.S. Pat. No. 5,330,899, which is incorporated herein by reference. Generally, inoculation devices 14 each include a gripping end 20 which may take the form of a socket (FIGS. 10 and 11) for receiving the lower gripping end of the handle. As will be appreciated, however, the handle also could fit over an upper end of the loops in order to grip the same, as shown in FIG. 11A. The function of inoculation devices 14 and their utility in inoculation techniques is discussed in more detail in the '899 patent.

Figure 2:
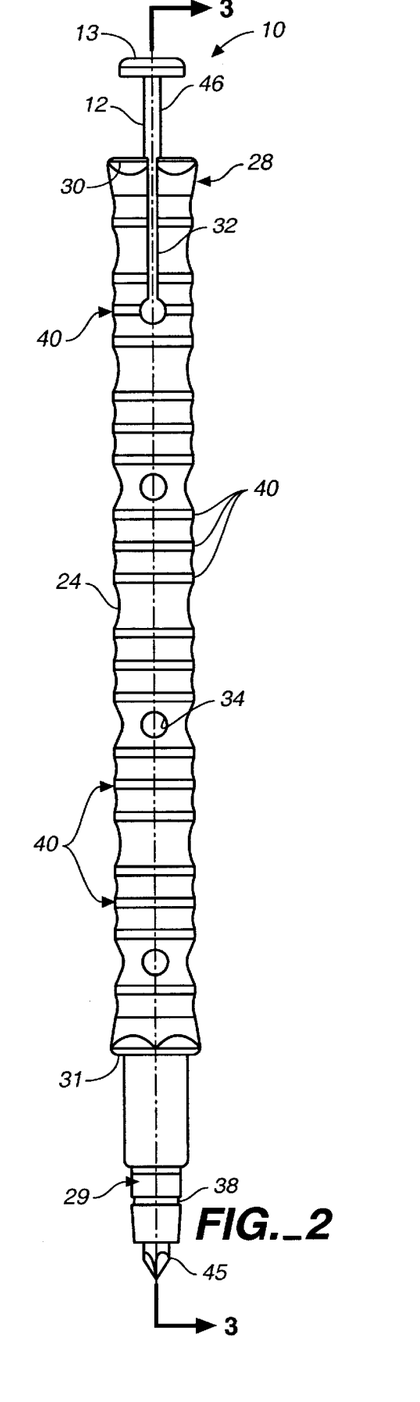
FIG. 2 is a side elevation view of the handle with the plunger in a retracted position.
Figure 3:
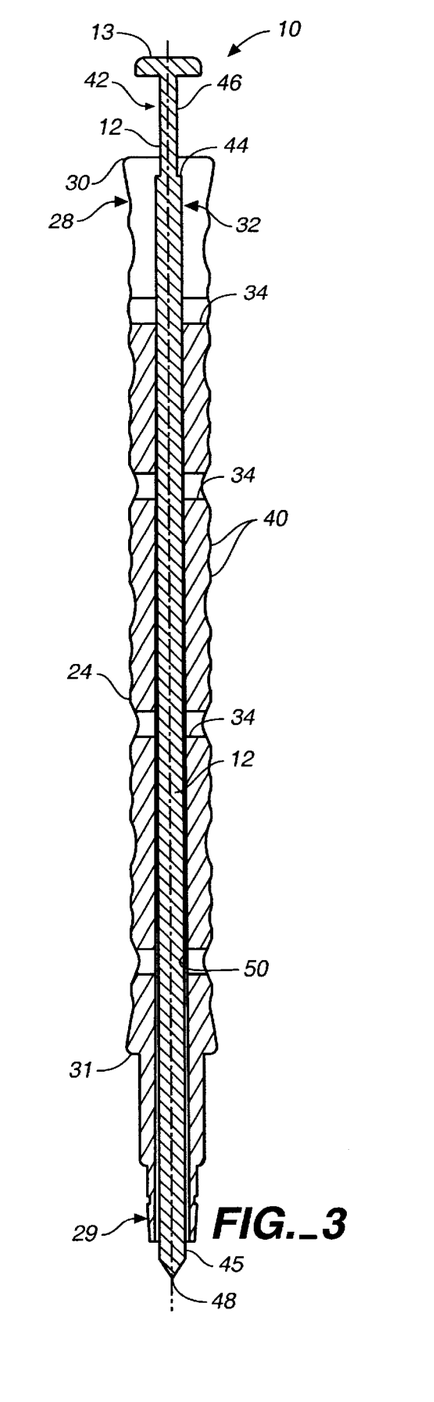
FIG. 3 is a sectional view, taken substantially along the lines 3—3 of FIG. 2.

Referring to FIGS. 2 and 3, body 24 of handle 10 is a one-piece, monolithically formed elongated tubular barrel that has an axial bore 50 extending through the full length of the body. An upper end 28 of body 24 includes an enlarged, hexagonal flanged edge 30, and similarly lower end 29 of body 24 includes and an enlarged, hexagonal flanged edge 31, which edges are discussed in more detail in connection with FIG. 8. Upper end 28 also includes a pair of relatively short, opposed longitudinally extending slots 32, which extend from the upper end 28 to the first of a series of radially extending holes 34. Longitudinal slots 32 function to permit radially outward expansion of the axial bore at upper end 28 of the body, which expansion opens up axial bore 50 for easy insertion of plunger 12 into body 24, which assembly is discussed in more detail in connection with FIGS. 2–6. Radial holes 34 extend transversely through to axial bore 50 of body 24 and are provided to enhance dimensional stability during injection molding and to improve cooling of the handle after autoclaving. It is preferred to provide a set of four radial holes substantially equally spaced, but more or fewer holes could be provided, depending on the size of the handle, handle material, and the particular autoclaving heating requirements.

The lower end 29 of body 24 includes an annular groove 38 that is formed for releasable mounting of a microorganism manipulating device, such as an inoculation loop. Specifically, annular groove 38 is designed to engage and releasably receive an annular rib 58 (FIG. 11) on the interior of the socketed gripping end 20 of the inoculation loop. The mating rib and groove secure loop 14 on handle 10 in a firm, frictional interference fit that permits the handle to manipulate the inoculation loop in a controlled manner. A reversal of parts, wherein the handle is formed to overfit and engage an end on the loop, rather than a socket, is shown in FIG. 11A.

Body 24 also includes a series of intermittently spaced raised annular ribs 40, positioned longitudinally between hexagonal edges 30, 31, which are provided to enhance gripping of body 24 by the hands of a technician. The diameter of hexagonal edges 30, 31 is greater than the diameter of annular ribs 40, so that when handle 10 is laid on a flat surface, the flat segments of hexagonal edges 30, 31 contact the flat supporting surface and prevent rolling of the handle.

Plunger 12 is a one-piece, monolithically formed cylindrical rod that is sufficiently narrow to fit in sliding relation to axial bore 50 of body 24, and plunger 12 also is longer than body 24. An upper end 42 of plunger 12 includes a shoulder 44 (FIGS. 4, 7 and 9) formed by a narrow diameter section 46 of the plunger. Plunger shoulder 44 can be positioned at any point along the length of the plunger, but preferably is formed in close proximity to upper plunger end 42. The purpose of shoulder 44 is discussed later. A lower end 45 of plunger 12 may be formed with a pointed tip 48, which is adapted to engage or push against inoculation loop socket wall 56 (FIG. 11)in order to eject the loop from the lower end of the handle. Tip 48 also preferably is pointed to assist in initially pushing through frangible membrane or foil sheet 19 which covers the upper ends of rack pockets 21 to maintain the sterile condition of the loops.

Figures 4, 7, 9:
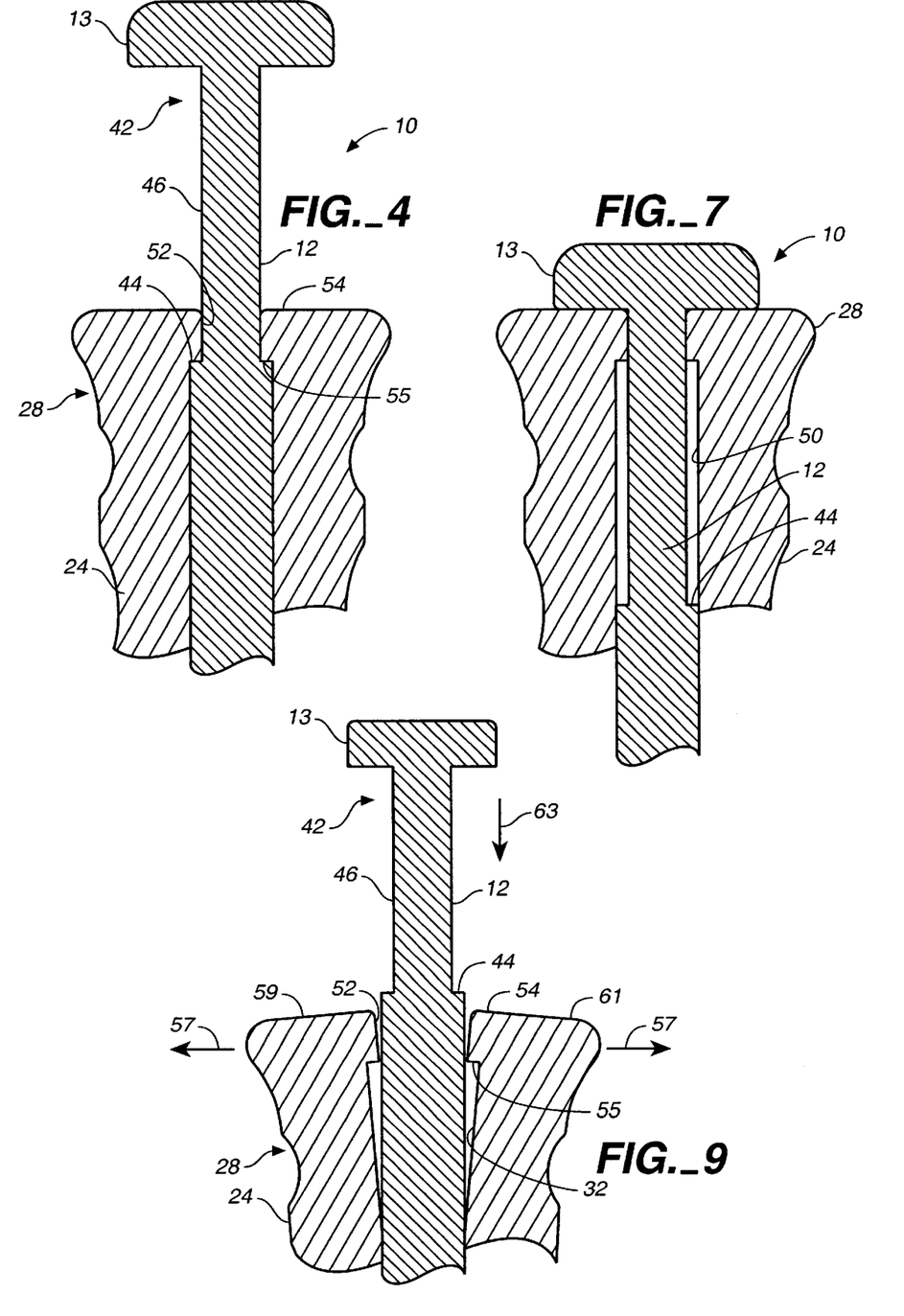
FIG. 4 is an enlarged, fragmentary, sectional view of the upper end of the handle of FIG. 2 with the plunger fully retracted.
FIG. 7 is an enlarged, fragmentary, sectional view of the handle of FIG. 2 with the plunger fully extended.
FIG. 9 is an enlarged, fragmentary, sectional view of the upper end of the body of the handle with the plunger in the process of being permanently assembled into the body.

FIGS. 2–4 show plunger 12 in its fully retracted position. It can be seen from these figures that the length of plunger 12 in the embodiment of FIGS. 1–11 is greater than the length of body 24, so that lower end 46 of plunger 12 extends beyond lower end 29 of body 24, even in the plunger's fully retracted position. Extension of plunger end 45 beyond lower body end 29 at full retraction, however, is not required for proper operation of the handle assembly.

Referring to FIG. 3, the diameter or width of axial bore 50 is slightly greater than the diameter or width of plunger 12, so that plunger 12 can easily slide within body 24 with minimal resistance when sliding between its retracted and its extended positions. When fully retracted, as shown in FIGS. 2 and 3, plunger 12 has its lower end 45 positioned proximate lower end 29 of body 24 and in an out-of-way position for mounting of a microorganism manipulation device to the lower end of body 24 without the plunger interfering with mounting. This feature is discussed in more detail with reference to FIG. 10.

Referring to FIG. 4, the upper end of handle 10 is shown in greater detail with plunger 12 in a fully retracted position. However, regardless of which position the plunger is in, its upper end 42 extends exteriorly of upper end 28 of body 24, with finger pad 13 always exterior of the body. The reduced diameter section 46 of plunger 12 extends between finger pad 13 and plunger shoulder 44 and is sized to fit closely within a narrow diameter bore 52 formed by an annular neck portion 54 of upper end 28 of body 24. Neck portion 54 defines a body shoulder 55 that faces plunger shoulder 44. Plunger shoulder 44 engages body shoulder 55 when plunger 12 is fully retracted, which limits upward movement of the plunger beyond its retracted position, i.e., the interengaging shoulders 44 and 55 prevent the plunger from sliding out of upper end 28 of the handle body.

Figure 5:
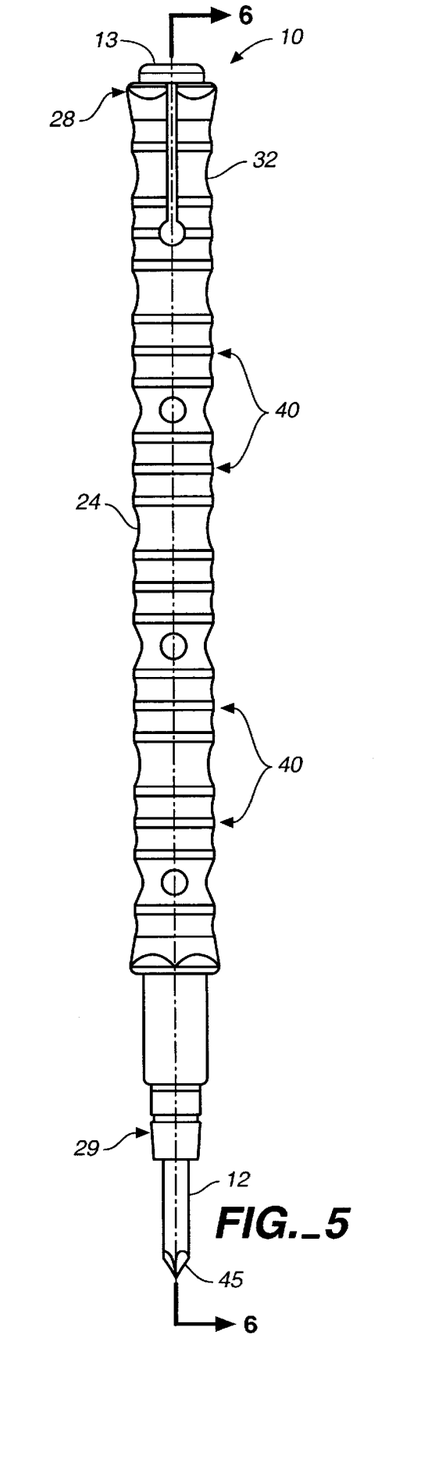
FIG. 5 is a side elevation view of the handle corresponding to FIG. 2 with the plunger fully extended.
Figure 6:
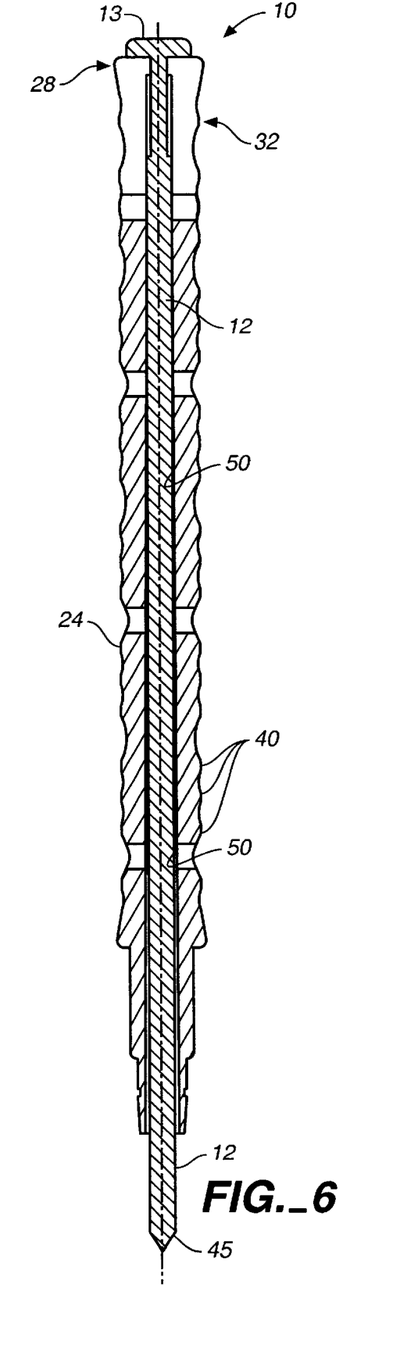
FIG. 6 is a sectional view, taken substantially along the lines 6—6 of FIG. 5.

Referring to FIGS. 5–7, shown is handle 10 with plunger 12 in its fully extended position. When the plunger is fully extended, finger pad 13 engages upper end 28 of body 24, as shown in FIG. 7, which engagement limits downward movement of plunger 12 beyond its fully extended position. In addition, when fully extended, as shown in FIGS. 5 and 6, lower end 45 of plunger 12 extends outwardly of lower end 29 of body 24. As discussed in more detail later, when plunger 12 is pushed to its fully extended position, its lower end 45 engages and ejects an inoculation loop carried by body end 29.

Figures 8, 10:
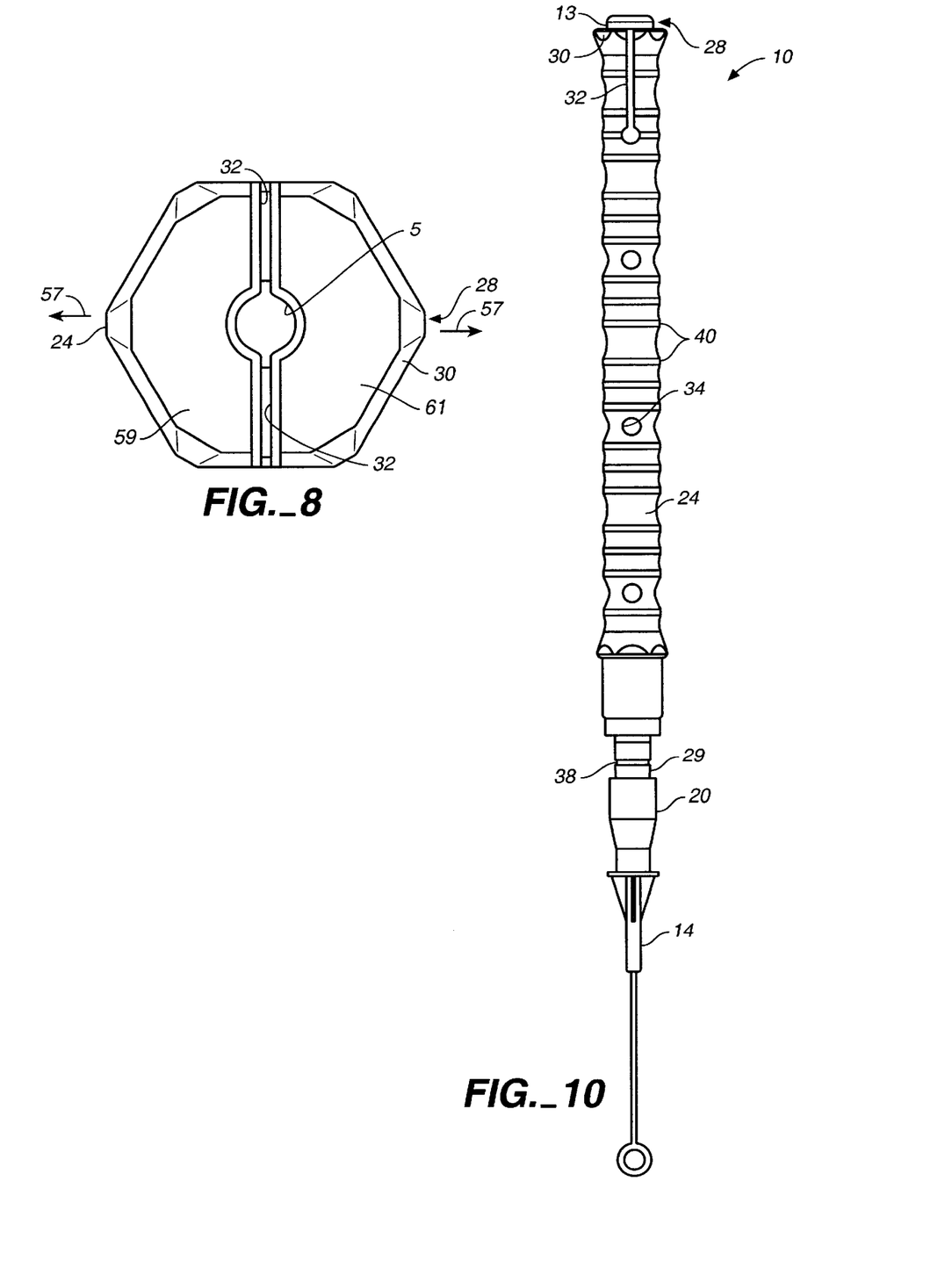
FIG. 8 is an enlarged top plan view of the body of the handle of FIG. 2.
FIG. 10 is a side elevation view of the handle of FIG. 2 with an inoculation loop in the process of being ejected from or attached to the handle.

Referring to FIG. 8, the hexagonal shape of upper edge 30 of body 24 is illustrated in greater detail. As discussed earlier, the flat side segments of edge 30 (as well as lower edge 31) prevent the handle from rolling when laid on a flat surface. Also shown in FIG. 8 are the opposed positions of longitudinal slots 32, which extend radially from the exterior of body 24 to axial bore 50 of the body and by design create a left half 59 and a right half 61 of upper end 28 of body 24. Left half 59 and right half 61 can flex outwardly, in the directions indicated by arrows 57, which provides the necessary resilient expansion of neck portion 54 in the upper end of the body that allows for insertion of plunger 12 into axial bore 50.

As illustrated in FIG. 9, when plunger 12 is inserted into body 24 upon initial assembly, in the direction indicated by arrow 63, longitudinal slots 32 allow upper body halves 59, 61 to flex outwardly, in the direction of arrows 57, which expands bore portion 52 defined by neck portion 54. During assembly, the wider diameter of plunger 12 below shoulder 44 pushes outwardly on halves 59, 61, causing them to move apart and thereby enlarge bore 52 at the upper end of the body. Once plunger shoulder 44 moves past neck portion 54 and body shoulder 55, the plunger and body are operably assembled for use in handling inoculation loops.

For use with inoculation devices of the type described in my aforementioned '899 patent, plunger 12 can have a travel stroke of approximately 0.383 inches. However, the travel of plunger 12 is dictated primarily by the design of the inoculation device as well as the lower end of the handle body. The travel between the retracted and extended positions needs to be sufficient to allow the socketed gripping end of the inoculation device to be inserted until rib 58 (FIG. 11) seats in groove 38, while enabling plunger end 48 to force rib 58 out of groove 38 and off of lower end 29 of the body.

Figure 11:
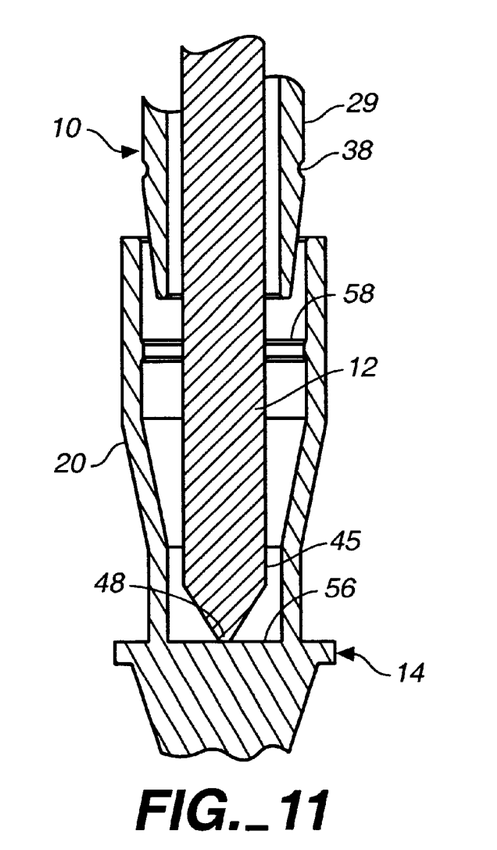
FIG. 11 is an enlarged, fragmentary, sectional view of the lower end of the handle of FIG. 2 with the plunger in the fully extended position to eject the inoculation loop from the handle.
Figure 11A:
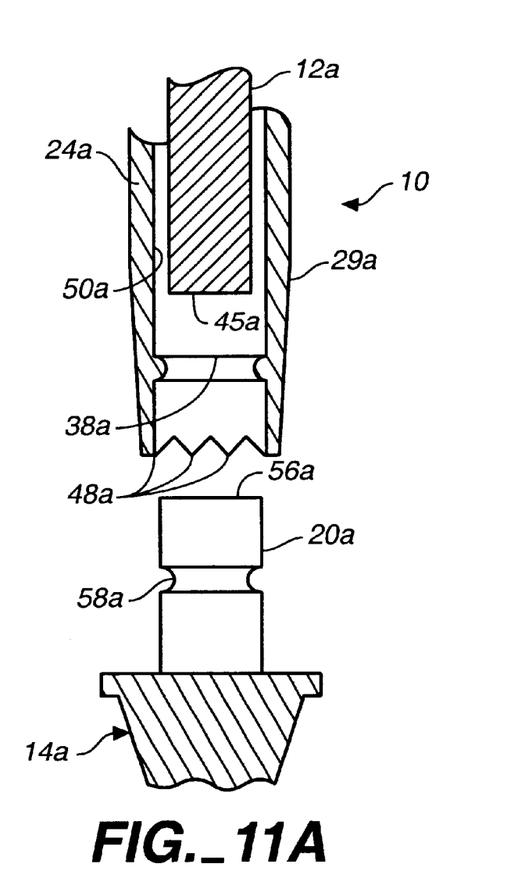
FIG. 11A is an enlarged, fragmentary sectional view corresponding to FIG. 11 of an alternative embodiment of the handle of the present invention and a modified inoculation loop.

FIGS. 10 and 11 show handle 10 with an inoculation device 14 being ejected off the handle. To eject a fully mounted inoculation device 14, plunger 12 is pushed down by a technician until finger pad 13 contacts upper end 28. As the finger pad depresses the plunger, lower tip 48 of the plunger contacts an interior wall 56 of the mounting socket of inoculation device 14, causing interior socket rib 58 of loop 14 to release from annular handle groove 38 thereby pushing the inoculation device off of the handle. Once removed, inoculation device 14 is typically discarded and the handle is reused with another inoculation loop. It will be understood that other releasable securement structures could be employed to mount loops 14 to handle 10, for example, the loop sockets could be grooved and the end 29 of the handle ribbed.

In FIG. 11A, an alternative embodiment of the handle is shown which is suitable for use with loops that have rod-like coupling ends rather than sockets. Handle 10a includes a body 24a with a lower end 29a and a bore 50a therethrough into which plunger 12a is reciprocally mounted. An inoculation loop 14a is formed with a rod-like upper end 20a, and bore 50a is dimensioned to slidably telescope over upper end 20a.

In order to releasably secure the loop to the handle, the rod-like end and the interior bore of the handle end are preferably formed with a mating rib and groove structure. As shown in FIG. 11A, a rod-like end 20a is formed with a groove 58a which mates with a rib 38a in bore 50a of the handle. The bore could be formed with the rib and end 20a formed with a groove.

As also will be seen, body end 29a of handle 10a includes a series of sharp teeth 48a which can be used to facilitate punching through frangible diaphragm 19 on the loop rack or case to pick up the loops.

Handle 10a additionally is provided with a plunger 12a that is shorter than plunger 12 and never extends from end 29a of the handle body. Instead, plunger end 45a will engage rod end 56a while the end still is inside bore 50a and displace the loop downwardly by an amount releasing groove 58a from rib 38a to eject the loop. The stroke of plunger 12a and its method of mounting inside the handle body are the same as described in connection with handle 10 and plunger 12.

In the extended position for plunger 12a, however, plunger end 45a does not need to extend beyond teeth 48a, only enough to disengage the loop and handle attachment structure.

The handle assembly of the present invention can be injection molded as only two pieces. Preferably, a structural plastic that can be autoclaved, such as acetal or nylon, is used to form the handle pieces. The most preferred material is an acetal copolymer sold by Celanese AG under the mark CELCON. Molding costs and complexity are reduced and assembly costs also are greatly reduced. The plunger can be easily inserted into the body and the neck-down upper end of the body snaps around the reduced diameter plunger upper end to capture and hold the plunger in the body for reciprocal movement between the retracted and extended positions.

The foregoing descriptions of a specific embodiment of the present invention have been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto when read and interpreted according to accepted legal principles such as the doctrine of equivalents and reversal of parts.

The invention claimed is:

1. A handle assembly for an inoculation loop, comprising:
   an elongated body having an upper end and a lower end and an axial bore therethrough, and
   an elongated plunger mounted for longitudinal movement within the axial bore of the body between an extended position and a retracted position,
   the plunger further including a transversely extending finger pad at the upper end of the plunger for hand manipulation by a user for limitation of the movement of the plunger beyond its extended position, and a plunger shoulder spaced along the length of the plunger from said finger pad,
   the body including a resilient, slotted upper end formed for enlargement of the axial bore at the upper end of the body for insertion of the plunger into the axial bore, and a narrow diameter section providing a body shoulder for engaging the plunger shoulder to limit movement of the plunger beyond its retracted position.

2. The handle assembly of claim 1 wherein, the plunger is a one piece monolithically formed member.

3. The handle assembly of claim 1 wherein, the body is a one piece monolithically formed member.

4. The handle assembly of claim 1 wherein, the body and the plunger are injection molded of structural plastic.

5. The handle assembly of claim 4 wherein, the structural plastic is acetal.

6. The handle assembly of claim 1 wherein, the narrow diameter section of the body is a neck portion at the upper end of the body, and the axial bore is formed with a diameter from the neck portion to the lower end adapted to permit removal of an injection molding core pin from the lower end of the body.

7. The handle of claim 1 wherein, the body includes at least one edge having a polygonal cross-section in order to resist rolling of the handle when laid on a flat surface.

8. The handle of claim 1 wherein, the body includes annular ribs to assist gripping of the body by a user.

9. The handle of claim 1 wherein, the body includes at least one radial hole extending through the body to the axial bore thereof.

10. The handle of claim 9 wherein, a plurality of radial holes are provided, each extending through the body to the axial bore thereof.

11. The handle of claim 10 wherein, the plurality of radial holes are spaced along the length of the body.

12. The handle of claim 1 wherein, the resiliently slotted upper end of the body includes a pair of longitudinally extending slots on opposite sides of the axial bore of the body.

13. The handle of claim 12 wherein, the body includes at least one radial hole extending transversely through the body through the axial bore, and the longitudinally extending slots extend along the length of the body to the radial hole.

14. The handle assembly of claim 1 wherein, the lower end of the body is formed for releasable mounting of a microorganism manipulating device thereto and the lower end of the plunger is formed to engage the microorganism manipulating device in order to eject the microorganism manipulating device off the lower end of the body when the plunger is moved to the extended position.

15. The handle assembly of claim 14 wherein, the lower end of the body is formed for insertion into a socket provided on an upper end of an inoculation loop.

16. The handle assembly of claim 14 wherein, the lower end of the body is formed for positioning over a rod-like upper end provided on an inoculation loop.

17. The handle assembly of claim 14 wherein, the plunger is positioned for mounting of the microorganism manipulating device to the handle when in the retracted position.

18. The handle assembly of claim 1 wherein, the plunger includes a narrow diameter length between the finger pad and the plunger shoulder.

19. The handle assembly of claim 1 wherein, one of the body and the plunger is formed with a pointed end thereon suitable for puncturing a frangible diaphragm covering a loop storage rack.

* * * * *